United States Patent [19]

Thakur

[11] Patent Number: 4,917,878
[45] Date of Patent: Apr. 17, 1990

[54] NOVEL USE OF A RADIOLABELLED ANTIBODY AGAINST STAGE SPECIFIC EMBRYONIC ANTIGEN FOR THE DETECTION OF OCCULT ABSCESSES IN MAMMALS

[75] Inventor: Madhukar L. Thakur, Cherry Hill, N.J.

[73] Assignee: Thomas Jefferson University, Philadelphia, Pa.

[21] Appl. No.: 189,141

[22] Filed: May 2, 1988

[51] Int. Cl.$^4$ .................... A61K 49/02; A61K 39/395
[52] U.S. Cl. .................................... 424/1.1; 424/85.91
[58] Field of Search ............................ 424/1.1, 85.91

[56] References Cited

U.S. PATENT DOCUMENTS

| | | | |
|---|---|---|---|
| 4,152,410 | 5/1979 | Ishii | 424/1.1 |
| 4,421,735 | 12/1983 | Haber et al. | 424/1.1 |
| 4,427,646 | 1/1984 | Olexa | 424/1.1 |
| 4,434,151 | 2/1984 | Byrne et al. | 424/1.1 |
| 4,444,744 | 4/1984 | Goldenberg | 424/1.1 |
| 4,460,561 | 7/1984 | Goldenberg | 424/1.1 |
| 4,479,930 | 10/1984 | Hnatowich | 424/1.1 |
| 4,575,556 | 3/1986 | Byrne et al. | 549/63 |
| 4,596,769 | 6/1986 | Shockman et al. | 424/1.1 X |
| 4,622,420 | 11/1986 | Meares et al. | 562/443 |
| 4,634,586 | 1/1987 | Goodwin et al. | 424/1.1 |
| 4,636,380 | 1/1987 | Wong | 424/1.1 |
| 4,647,445 | 3/1987 | Lees | 424/1.1 |
| 4,652,519 | 3/1987 | Warshawsky et al. | 435/7 |
| 4,668,503 | 5/1987 | Hnatowich | 424/1.1 |
| 4,671,958 | 6/1987 | Rodwell et al. | 424/85 |
| 4,678,667 | 7/1987 | Meares et al. | 424/85 |
| 4,707,352 | 12/1987 | Stavrianpoulos | 424/1.1 |
| 4,724,212 | 2/1988 | Epstein | 424/1.1 X |
| 4,724,213 | 2/1988 | Epstein | 424/1.1 X |

OTHER PUBLICATIONS

Solter, et al., "Monoclonal Antibody Defining a Stage-Specific Mouse Embryonic Antigen", (SSEA-1), Proc. Natl. Acad. Sci., USA, vol. 75, No. 11, pp. 5565-5569, Nov. 1978.
Thakur, et al., Journal of Nuclear Medicine, vol. 18: 1014-1019 (1977).
Thakur, et al., Nucl. Med. Biol., vol. 14: 51-58 (1987).
Thakur, Research in Progress: FY 1986, Summaries of Projects Sponsored by the Office of Health and Environmental Research, Office of Scientific and Technical Information, Jan. 1986.
Richard and Thakur, J. Nucl. Med., vol. 28: Abstract No. 693 (1987).
Thakur, et al., J. Nucl. Med., vol. 28: Abstract No. 419, (1987).
Locher, et al., Nuclear Medicine Communications, vol. 7: 659-670 (1986).
Solter and Knowles, Proc. Nat'l Acad Sci. USA, vol. 75: 5565-5569 (1978).
Fredriksson, et al., Protein A-Sehparase Cl-4B Affinity Purification of IgG Monoclonal Antibodies from Mouse Ascites, S-751 82, Uppsala, Sweden 1985.
De Riemer, et al., J. Labeled Compounds in Radiopharmaceuticals, vol. XVIII: 1517-1534 (1981).
Rodwell, et al., Proc. Nat'l Acad. Sci. USA, vol. 83: 2632-2636.
Meares, et al., Anal. Biochem., vol. 142: 68-78 (1984).
Feldman, Anal. Biochem., vol. 48: 317-338 (1972).
Intenzo, et al., J. Nucl. Med., vol. 28: 438-441 (1987).
Schrothe, Eurp. J. Nucl. Med., vol. 6: 469-472 (1981).

Primary Examiner—John S. Maples
Attorney, Agent, or Firm—Woodcock Washburn Kurtz Mackiewicz & Norris

[57] ABSTRACT

The invention discloses improved reagents containing antibodies against stage specific embryonic antigen-1 antibodies and improved methods for detection of occult abscess and inflammation using the improved reagents.

10 Claims, No Drawings

NOVEL USE OF A RADIOLABELLED ANTIBODY AGAINST STAGE SPECIFIC EMBRYONIC ANTIGEN FOR THE DETECTION OF OCCULT ABSCESSES IN MAMMALS

REFERENCE TO GOVERNMENT GRANTS

The invention described herein was supported by Department of Energy grant DE-FG02-85ER60295 and in part by NIHCA grant 05137-10. The United States Government has certain rights in the invention.

BACKGROUND OF THE INVENTION

The invention relates to the field of radioimaging and more particularly to immunoreagents and methods for detecting neutrophils at the site of occult abscesses.

Hidden infections and inflammations or occult abscesses are difficult to detect by conventional methods. Often an infection in the patient is diagnosed by an elevated white cell count or the presence in the blood of a specific pathogen, but the exact location of the infection can not be found by manual examination. X-ray of the patient is usually not helpful because the infection or inflammation is in soft tissue which is not detected by this method. Delay in detecting occult abscesses delays treatment of the condition and increases the risk of exacerbation and spread of the infection or inflammation.

New methods of detecting occult abscesses which are not time consuming and which accurately locate the infection or inflammation are needed to overcome the difficulties of detecting these conditions by conventional methods.

Radiolabels such as $^{111}$Indium and $^{67}$Gallium have been used to make body tissues radiodense and thus appear on X-ray film. This method however lacks specificity and labels many types of tissues. A high background of radioactivity is produced so that the target tissue cannot be distinguished from the background.

Thakur et al., Journal of Nuclear Medicine 18: 1014–1019, (1977) used $^{111}$Indium-oxine to label leukocytes. In this method a sample of the patient's blood is removed and the leukocytes separated from the rest of the blood. The leukocytes are then labeled with $^{111}$Indium oxine and reinjected into the patient. The radiolabeled leukocytes are then allowed to migrate to sites of occult abscesses. The radiolabeled leukocytes are then detected by scintigraphic methods. The $^{111}$Indium-oxine method is time consuming, delaying rapid diagnosis of the occult abscess. It also requires highly skilled personnel and specialized facilities to perform the separation and labeling. Additionally, the radiolabeled leukocytes must be quickly used or they will not be viable.

Antibodies are known for various purposes such as localization of tumors, detection of vascular clots and detection of infection and inflammation. Monoclonal antibodies produced from hybridomas are often used in these methods because of the specificity with which they will bind to target molecules and cells.

Thakur et al. Nucl. Med. Biol. 14: 51–58, 1987, evaluated the use of radiolabeled monoclonal antibodies specific for human platelet antigenic determinants to detect thrombi.

In Thakur, Research in Progress: FY 1986 Summaries of Projects Sponsored by the Office of Health and Environmental Research, Office of Scientific and Technical Information, Jan. 1986, it is stated that Thakur will be developing methods of radiolabeling human neutrophils, platelets and lymphocytes selectively in whole blood.

In Richard and Thakur, J. Nucl. Med. 28: abstract no. 693, (1987), four bifunctional chelating agents were tested for binding with SSEA-1 antibodies as a tracer for human neutrophils.

Thakur et al. J. Nucl. Med. 28: abstract no. 419, (1987) evaluated bimane analogues for use as chelating agents for radiolabels and proteins.

Locher et al, Nuclear Medicine Communications 7: 659–670, (1986) used radiolabeled monoclonal antibodies directed against human granulocytes to detect inflammatory and infectious lesions. These researchers intravenously infused $^{123}$Iodine labeled monoclonal antibodies and waited for them to accumulate at a suspected area of infection. The radiolabel was then detected using a gamma camera. Areas of infection were located at expected sites.

U.S. Pat. 4,634,586 issued Jan. 6, 1987 to Goodwin and Meares discloses a reagent and method for radioimaging leukocytes. In this method leukocytes are radioimmunoimaged by injecting patients with an immunoreactive nonleukocidal conjugate of an anti-leukocyte antibody and a gamma-emitting radioactive metal chelate, waiting for the conjugate to localize on the leukocytes, injecting the patient with an antibody to the conjugate to clear the blood of background nonlocalized conjugate and visualizing the leukocytes by scintillation scanning. The method can also be used without the step of injecting an antibody to clear background nonlocalized antibody.

U.S. Pat. 4,636,380 issued Jan. 13, 1987 to Wong discloses a method of directly labeling proteinaceous substances with $^{111}$Indium or $^{111}$Indium for use in scintigraphic imaging of thrombi, emboli, infectious lesions, tumors, myocardial infarction and vascular abnormalities.

U.S. Pat. 4,444,744 issued April 24, 1984 to Goldenberg discloses the use of radiolabeled antibodies to tumor cell surface antigens for the detection, localization and therapy of tumors.

U.S. Pat. 4,460,561 issued July 17, 1984 to Goldenberg discloses the use of radiolabeled antibodies specific intracellular tumor-associated markers for the detection, localization and therapy of tumors.

Other U.S. Pats. such as 4,427,646 (Olexa et al.) and 4,647,445 (Lees) disclose the use of radiolabeled proteins or lipoproteins in radiographic detection of illness.

Agents and methods useful for associating the an antibody or other protein to a radiolabel have been disclosed in various U.S. patents.

U.S. Pat. 4,479,930 issued Oct. 30, 1984 to Hnatowich discloses methods of coupling amines such as polypeptides and proteins to radiolabels using a dicyclic dianhydride of compounds such as ethylenediaminetetraacetic acid or diethylenetriaminepentaacetic acid. The patent also discloses chemical compositions containing the chelating agents and proteins or polypeptides.

U.S. Pat. 4,668,503 issued May 26, 1987 to Hnatowich discloses a process for labeling amines such as antibodies, proteins and polypeptides with $^{99m}$Technetium in the presence of a stannous reducing agent.

U.S. Pat. 4,622,420 issued Nov. 11, 1986 to Meares et al. discloses chelating agents which are analogs of ethylenediaminetetraacetic acid, ethylenediaminetriacetic acid or ethylenediaminepentaacetic acid which are useful in attaching radiolabels to biological molecules such as proteins.

Other U.S. Pats. such as 4,678,667 (Meares et al.), 4,707,352 (Stavrianpoulos), 4,421,735 (Haber et al.), 4,434,151 (Byrne et al.) and 4,575,556 (Byrne et al.) also disclose chelating agents which can be used to link proteins such as antibodies and radiolabels for use in detecting pathological conditions.

U.S. Pat. 4,652,519 issued March 24, 1987 to Warshawsky et al. discloses bifunctional chelating agents which can be used in radioimmunoassays and the like.

U.S. Pat. 4,671,958 issued June 9, 1987 to Rodwell et al. discloses polypeptide linkers for use in linking antibodies and compounds such as therapeutic compounds and radiopharmaceuticals which are then transported to target locations in the body.

Although some of these methods may detect infections and inflammations, improved immunoreagents which are specific for cell types such as neutrophils which accumulate at sites of infection and inflammation but which will not bind to other types of cells in appreciable amounts and give high background readings are still needed. Accordingly, it is an object of the invention to provide improved methods and reagents for detecting occult abscesses and inflammation. It is also an object of the invention to provide improved reagents for the detection of occult abscesses and inflammation which have a high specificity for neutrophils, a type of granulocyte cell which accumulates at the site of infection or inflammation.

SUMMARY OF THE INVENTION

The present invention provides improved methods of detecting occult abscess and inflammation in mammals. An effective amount of a reagent comprising antibody against stage specific embryonic antigen-1 (hereinafter "SSES-1), a radiolabel and a bifunctional chelating agent which links the antibody and the radiolabel is injected into the mammal under conditions which allow the reagent to accumulate at sites of occult abscess. Occult abscess is then detected by radiographic method. The bifunctional chelating agent is preferably cyclic anhydride of diethylenetriaminepentaacetic acid (DTPA). The radiolabel may be $^{111}$Indium, $^{99m}$Technetium, $^{67}$Gallium, $^{68}$Gallium, $^{97}$Ruthenium, $^{123}$Iodine, $^{90}$Yttrium, $^{203}$Lead, $^{67}$Copper or $^{111m}$Indium, $^{111}$Indium and $^{99m}$Technetium are the preferred radiolabels. The preferred radiographic method for use in the invention is scintillation scanning.

The present invention further provides improved reagents for use in a method of detecting occult abscess and inflammation in a mammal wherein a reagent containing a radiolabeled antibody is injected into the mammal, the radiolabeled antibody is allowed to accumulate at the site of the abscess and the radiolabel is then detected. The improved reagents comprise antibody against SSEA-1, a radiolabel and a bifunctional chelating agent to link the antibody and the radiolabel. The preferred bifunctional chelating agent is cyclic anhydride of diethylenetriaminepentaacetic acid (DTPA). The radiolabel may be $^{111}$Indium, $^{99m}$Technetium, $^{67}$Gallium, $^{68}$Gallium, $^{97}$Ruthenium, $^{123}$Iodine, $^{90}$Yttrium, $^{203}$Lead, $^{67}$Copper or $^{111}$Indium. $^{111}$Indium and $^{99m}$Technetium are the preferred radiolabels.

The invention further provides additional improved reagents for use in methods of detecting occult abscess and inflammation in a mammal wherein a reagent containing an antibody linked to a chelating agent and a radiolabel is administered to the mammal, the reagent is allowed to accumulate at the site of the abscess and the radiolabel is then detected by radiographic method. Anti-stage specific embryonic antigen-1 antibody is used in the reagent in these methods.

Subsequent to administration of the reagent containing the radiolabeled antibody into the mammal, it is believed that the antibody in the reagent binds to neutrophils in the bloodstream of the mammal. It is believed that neutrophils labeled with the reagent will then migrate towards areas of infection or inflammation. Neutrophils are known to accumulate at sites of infection and inflammation and thus the accumulation of labeled neutrophils at a particular site signals the presence of infection or inflammation. The radiolabel is then detected using radiographic method. Accumulation of the radiolabel in tissues corresponds to the presence of infection or inflammation.

The SSEA-1 antigen has been found to be expressed in various normal human tissues. The antigen has been found on granulocytes, their precursors, brain, stomach, colon, breast, adrenal gland, salivary gland, bladder and kidney, but not on the liver, erythrocytes or lymphocytes. SSEA-1 has also been found on several mouse tissues especially kidney and brain, but not on neutrophils. Furthermore, in the mouse there was no significant retention of radiolabeled antibodies to SSEA-1 when injected in vivo. When anti-SSEA-1 antibodies were conjugated with DTPA and labeled with $^{111}$Indium and mixed with whole human blood, 27% of the antibodies bound to polymorphonuclearleukocytes (neutrophils), 28% bound to red blood cells and 44% remained in the plasma. When mixed with separated human blood cells, i.e. leukocytes or neutrophils and plasma only, 81.3% of the labeled antibody bound to neutrophils and 18.7% remained in the plasma. Anti-SSEA-1 antibodies have a neutrophil specificity of $10^{-11}$ M. Thus, due to the abundance of in vivo neutrophils and the high specificity of anti-SSEA-1 antibodies for neutrophils, the use of anti-SSEA-1 antibodies in methods and reagents for detecting occult abscesses and inflammations should allow more accurate and specific detection of occult abscesses and inflammation than reagents and methods heretofore described.

DETAILED DESCRIPTION OF THE INVENTION

Anti-stage specific embryonic antigen-1 (SSEA-1) is an IgM monoclonal antibody produced by immunizing mice with murine embryonal carcinoma F9 cells according to the method of Solter and Knowles, Proc. Natl. Acad. Sci. USA 75: 5565–5569, (1978). The anti-SSEA-1 monoclonal antibody, produced from the hybridoma MCA 480 (Wistar Institute, Philadelphia, Penna.) is particularly useful in the practice of the invention.

The radiolabeled antibody reagent is preferably intravenously infused into the mammal. For infusion into the mammal, the radiolabeled antibody is mixed with a suitable injection vehicle such as normal saline solution or human serum albumin. The radiolabeled antibody is allowed to accumulate at the site of occult abscess. Maximum accumulation of the radiolabeled antibody at the site of occult abscess or inflammation may take up to 24 hours after administration of the radiolabeled antibody; however, detection of an occult abscess may be done before the end of 24 hours. The occult abscess is detected using conventional radiographic methods such as a gamma camera, single-photon emission computed tomograph (SPECT), positron emission computed tomograph and scintillation scanning. Scintillation scanning is the preferred method of detecting an occult abscess or inflammation.

Radiolabels such as $^{111}$Indium, $^{99m}$Technetium, $^{67}$Gallium, $^{68}$Gallium, $^{97}$Ruthenium, $^{123}$Iodine, $^{90}$Yttrium, $^{203}$Lead, $^{67}$Copper and $^{111m}$Indium are suitable for use in the invention. These radiolabels are commercially available. Radiolabels useful in the invention preferably have a short half life and are gamma emitters. $^{111}$Indium and $^{99m}$Technetium are preferred for use in the invention. These radiolabels have short half lives, are rapidly cleared from the body and are readily available in purified form.

Bifunctional chelating agents are suitable for use in the invention. The four chelating agents described herein are suitable for use in the invention. The preferred chelating agent is cyclic anhydride of diethylenetriaminepentaacetic acid (DTPA).

A dosage of the radiolabeled antibody which could be useful in the invention is from approximately 50 micrograms to approximately 4 milligrams per mammal. The larger figure represents a saturation rate of antibody molecules bound to polymorphonuclear leukocytes of approximately 4%. At this rate no changes in the phagocytic ability and nylon wool adherence of the cells was observed at this level. In an average normal adult human there is estimated to be approximately $10^{16}$ antigens available for the anti-SSEA-1 binding. At a rate of 4% saturation, 4 milligrams could be administered.

Antibodies

Nine murine antibodies, listed in Table-1 were obtained from the following sources. Anti-SSEA-1 (stage specific embryonic antigen-1), produced by the hybridoma MCA 480, was obtained from the Wistar Institute, Philadelphia, Penna. Antibody B.37.2.1 was also obtained from the Wistar Institute. Antibodies MCA 161, MCA 87, MCA 148, MCA 215 and MCA 167 were obtained from Serotec. FMC-11 was obtained from Sera-Lab. Antibody B.6.2 was obtained from the National Institutes of Health, National Cancer Institute. Some of the monoclonal antibodies (MAbs) were already purified, some of them were in ascites fluid and one was purified but contained added Bovine serum albumin as a stabilizer when received. The pure antibodies were used without further processing. Those in ascites fluid were separated using a Protein A Sepharose Cl-4B affinity column (0.3 cm × 15 cm) according to the procedure of Fredriksson et al. Protein A-Sehparose Cl-4B affinity purification of IgG monoclonal antibodies from mouse ascites. S-751 82 Uppsala, Sweden, 1985. The antibody in Bovine serum albumin was separated using Sephadex G-50 column and 0.1M NaHCO$_3$ pH 8.4 as an eluent. The eluent was monitored by a U.V. detector and fractionated using a fraction collector. The appropriate fractions were pooled and the MAb was concentrated using a microconcentrator (Centricon-30).

Labeling human neutrophils. Separated vs in whole blood:

Antibodies were labeled with $^{111}$In or $^{99m}$Tc. The MAb:DTPA molar ratio of 1:5 and the dithionite concentration of 0.2 ug/ul reaction volume (MAb:dithionite ratio of 1:3000) were chosen for labeling. The latter was used for reduction of $^{99m}$Tc$^{7+}$. Anticoagulated fresh venous blood was obtained from normal human volunteers. Depending upon the aim of the study, leukocytes or neutrophils were separated using the procedure of Thakur et al., J. Nucl Med. 18: 1012-1-19, (1977), and their number determined using a cell counter (ZM Coulter). Cells were suspended either in autologus plasma or in phosphate buffered saline pH 7.4. The radiolabeled antibody preparations were then added to the cell suspension in such a way that the MAb molecules would not saturate the cell surface antigens. A known quantity of radiolabeled MAbs were also added to a known volume of whole blood. Following incubation at 22° C. radioactivity associated with the neutrophils, and supernatant, or in the case of whole blood, the neutrophils, the erythrocytes and the plasma radioactivity was determined. On each occasion, the labeled neutrophils were washed with fresh autologus plasma at least once, to remove any unassociated radioactivity. The percentage of radioactivity associated with the cells was then determined. The results of several experiments are shown in Table 1.

TABLE 1

Evaluation of Human Neutrophil (PMN) Specific Antibodies Coupled with DTPA and Labeled with $^{111}$In

| MAb | Class | Separated Cells (%) | | Whole Blood (%) | | |
|---|---|---|---|---|---|---|
| | | PMN | Plasma | PMN | RBC | Plasma |
| Anti-SSEA-1 | IgM | 81.3 | 18.7 | 27.0 | 28.0 | 44.2 |
| B.37.2.1 | IgM | 72.4 | 27.6 | 37.9 | 25.2 | 36.9 |
| MCA 87 | IgG2a | 36.90 | 63.09 | 24.99 | 15.02 | 59.99 |
| MCA 149 | IgG1a | 15.34 | 84.66 | 14.57 | 16.30 | 69.13 |
| MCA 167 | IgG2a | 41.43 | 58.57 | 41.32 | 14.13 | 54.50 |
| MCA 215 | IgM | 17.16 | 69.05 | 14.13 | 10.45 | 75.42 |
| FMC 11 | IgG1 | 38.69 | 61.31 | | | |
| B.6.2 | IgG | 9.2 | 90.8 | | | |
| MCA 161 | IgG1 | 13.2 | 86.8 | 11 | 12.8 | 76.1 |

Chelating Agent Labeling with $^{111}$Indium $^{111}$Indium (Atomic Energy Canada 50mCi/ml HCl) was used in tests of chelating agents. Four bifunctional chelating agents were evaluated—the cyclic anhydride of diethylenetriaminepentaacetic acid (DTPA) (Sigma), ethylenediamine-di(o-hydroxyphenylacetic acid) (EDDHA) (Sigma), (S)-4-[2,3-bis[bis(carboxymethyl)amino]propyl]aniline (ABE) and (S)-N-4-[2,3-bis[bis(carboxymethyl)amino]propyl]phenyl bromoacetamide (BABE). ABE and BABE were prepared according to the method of DeRiemer et al, J. Labeled compounds in Radiopharmaceuticals, vol. XVIII, 517-1534, (1981). The purity of the newly synthesized ABE and BABE, before and after $^{111}$In labeling was examined with HPLC using Water's NOVA-PAK column and a mobile phase containing 4% acetonitrile, 2% methanol, and 2% gl. acetic acid in water. The HPLC equipped with both a U.V. detector and a NaI (Tl) crystal detector, each coupled to dual channel chart recorder, allowed us to identify the association of radioactivity with the absorbance peaks of ABE and BABE. Pure samples of ABE and BABE served as control.

ABE, BABE and EDDHA were dissolved in 0.9% NaCl, pH 7. DTPA was suspended (1 mg/ml) in dry metal free chloroform and sonicated for uniform particle size so that a calculated column of the suspension would represent the desired quantity of DTPA.

All MAbs (100 ug each time) used were either IgM or IgG and their molecular weight was assumed to be 900,000 or 150,000 daltons respectively. EDDHA, ABE (control) and BABE were used in protein to the agent molar ratios of 1:2.5, 1:3 and 1:3 respectively following the methods of Rodwell et al., Proc. Natl. Acad. Sci. USA 83: 2632-2636, (1986) and Meares et al. Anal. Biochem 142: 68-78, (1984).

When given a quantity of $^{111}$In anti-SSEA-1, prepared using ABE, BABE, EDDHA or DTPA as the bifunctional chelating agent was incubated with an equal number of isolated human neutrophils (suspended in plasma or phosphate buffered saline), 70% to 80% of the radioactivity was cell associated (Table 2). In whole blood, however, the quantity of neutrophil associated $^{111}$In-DTPA MAb averaged 27%, compared to that of only 3%-5% with $^{111}$In-ABE, $^{111}$In-EDDHA or $^{111}$In-BABE-MAB. In the cases of the latter three, the quantity of radioactivity that remained in plasma was greater than 75% as compared to approximately 40% with $^{111}$In-DTPA-MAb.

TABLE 2

Results of comparison of four bifunctional chelating agents (Anti-SSEA-1)
% $^{111}$In associated with (N = 4)

| Agent | Neutrophils | Erythrocytes | Plasma |
|---|---|---|---|
| (In whole blood) | | | |
| DTPA | 27.0 | 28.8 | 44.2 |
| EDDHA | 2.8 | 18.2 | 78.9 |
| ABE | 3.6 | 20.4 | 76.8 |
| BABE | 3.2 | 15.1 | 81.4 |
| (In separated cells) | | | |
| DTPA | 81.3 | — | 18.7 |
| EDDHA | 69.9 | — | 30.1 |
| ABE | 73.2 | — | 26.8 |
| BABE | 79.4 | — | 20.6 |

In order to determine the Mab:DTPA molar ratio that would provide the optimal radionuclide yield, yet would not drastically alter the biochemical specificity of the protein, a known quantity of DTPA was incubated with MAb in the molar ratio of 1:1 to 1:5. Unreacted was eliminated using the microconcentrator. DTPA-MAb was then labeled with $^{111}$Indium. $^{111}$In chloride was converted into the acetate form using 0.1 M Na-acetate buffer pH 6.1 according to the procedure of Thakur et al., J. Nucl. Med. Biol. 14: 51-58, (1987) before use. The labeled antibodies were then tested for any unbound $^{111}$In instant thin layer chromatography using 2 M Urea as a mobile phase.

One microgram of each of these labeled MAb (1 ug IgM = approximately 6.3 10$^{11}$ molecules) were the incubated each with approximately 10$^7$ isolated human neutrophils suspended in 1 milliliter plasma. Care was taken that the MAb molecules did not saturate the antigenic binding sites available on neutrophil surface. Following a 30 min. incubation at 22° C. the radioactivity associated with the neutrophils was determined and plotted as a function of MAb:DTPA molar ratio for the respective preparation. If the increased DTPA ratio resulted in the loss of the biological activity of the protein the quantity of MAb interacted with the cells may decrease.

A DTPA:MAb molar ratio of 1:1 to 5:1 did not alter the immunochemical activity of the protein as measured by the quantity of the $^{111}$In-DTPA-MAB associated with human neutrophils. In all subsequent preparation therefore a DTPA:MAb (IgM) ratio of 5:1 was used. Using this proportion, on the average, one DTPA molecule bound per MAb molecule was obtained. Determination of DTPA molecules per MAb molecule:

The number of DTPA molecules attached per MAb molecule were estimated using the indium carrier method of Thakur et al. J. Nucl. Med. Biol 14: 51-58, (1987). The radioactivity associated with the protein was determined, and the bound to free ratio, and the number of indium ions bound per MAb molecule were calculated. The data were plotted according to the method of Feldman, Anal. Biochem 48: 317-338, (1972), to determine the number of DTPA molecules bound per MAb molecule. Using a DTPA:MAb (IgM) ratio of 5:1, on the average, one DTPA molecule bound per Mab molecule was obtained.

Determination of Neutrophil Specificity:

The antigenic specificity of the MAb and the number of antigenic sites per human neutrophil were determined for B.37.2.1 and anti-SSEA-1 using $^{111}$In or $^{125}$I as tracers. Radioiodination was carried out according to the procedure of Thakur et al. J. Nucl. Med. Biol 14: 51-58, (1987), using Iodo-Gen (Pierce chemicals) as an oxidizing agent. The unbound radioactivity was eliminated and the quantity of MAb was determined spectrophotometrically. Neutrophils were separated from 100 ml anticoagulated blood freshly drawn from normal human volunteers and the cell concentration was determined using a ZM Coulter counter. Neutrophils were then divided equally into eight sterile plastic test tubes, each containing $2.8 \times 10^7$ cells in 0.5 ml plasma. To these were then added a known but increasing quantity of labeled MAb and allowed to incubate at 22° C. for 30 minutes. The cells were then centrifuged, washed once with plasma, centrifuged again and the corresponding supernatants combined. The quantity of the radioactivity associated with the cells was determined to estimate the number of MAb molecules bound per cell. The experiment was repeated and data were subjected to Scatchard plots and regression analysis for the best fit of the interception and x and y axis.

The neutrophil specificity was $2 \times 10^{-11}$M for B.37.2.1 and $1.6 \times 10^{-11}$M for anti-SSEA-1. The number of surface antigens was approximately $7.8 \times 10^5$ for B 37.2.1 and $5.1 \times 10^5$ for anti-SSEA-1 per cell.

Labeling DTPA-MAb with $^{99m}$Tc: The choice of reducing agents:

Since $^{99m}$Tc will bind to DTPA only in the reduced form, different reducing agents were tested for use with DTPA and the antibodies. Stannous chloride, ascorbic acid, sodium borohydride and dithionite were tested as reducing agents. To a known quantity of $^{99m}$TcO$_4$-solution in four groups of several test tubes were added an increasing quantity of the agents and allowed to incubate at 22° C. for 10 minutes under nitrogen atmosphere. These were then added to DTPA coupled anti-SSEA-1. The reducing agent to MAb ratios ranged from $8 \times 10^2$ to $8 \times 10^3$. Following a 15 minute incubation at 22° C., the MAb was separated free of unbound $^{99m}$Tc and the percentage of radioactivity associated with the protein was determined. The results were calculated and plotted as a function of the molar ratio and percent radioactivity associated with the protein. The absence of any unbound $^{99m}$Tc was confirmed by paper chromatography and HPLC.

For labeling DTPA conjugated MAb with $^{99m}$Tc, the use of dithionite gave the best results. 75-95% of the $^{99m}$Tc bound to DTPA. Sodium borohydride produced labeling in the range of 30 to 70%. Stannous chloride and ascorbic acid produced labeling in the range of 5 to 25%. 0.2 ug dithionite per ul reaction mixture was used in experiments for labeling 100 ug DTPA-IgM in 300 μl, giving a reducing agent to MAb molar ratio of 3000:1. Reducing $^{99m}TcO_4^{31}$ first enhances labeling, giving approximately the same yield as with $^{111}$In (70%–80%). Antibodies labeled with $^{99m}$Tc were also used to label human neutrophils in whole blood and results (28±5%) equivalent to those with $^{111}$In-DTPA-MAb were obtained.

Determining the optimal concentration of the reducing agent:

In a series of six clean test tubes, 200 uCi of freshly eluted $^{99m}$Tc was dispensed and volume of the solution was adjusted to 100 μl to 2 ml with 0.9% NaCl. Freshly prepared dithionite solution as then added to the test tubes in such a way that the reducing agent concentration ranged from 0.05 ug/ml to 0.8 μg/ml. Following a 10 min. incubation at 22° C., the radioactivity was transferred to corresponding number of test tubes each containing 100 up protein. The reaction mixture was then allowed to incubate for 15 mins. at 22° C. and filtered through Centricon devices (Amicon). The radioactivity in the filtrate, bound to the filter and associated with the protein was then measured and the percentages calculated. These were then plotted as function of dithionite concentration. A concentration of 0.2 ug dithionite per ul was found to give the highest amount of $^{99m}$Tc bound to protein and this concentration was used in experiments.

Cell viability following MAb labeling:

$^{111}$Indium DTPA coupled anti-SSEA-1 were used in this study. Approximately $9 \times 10^6$ human neutrophils separated using density gradient were suspended in 0.5 ml plasma in each of five test tubes. Four of these received 0.5 to 5 ug of the MAb. Assuming uniform and 100% interaction, the highest MAb concentration would bind 10% of all available neutrophil antigens. The cells in the fifth test tube served an control. Following a 30 min. 22° C. incubation, the cells in all test tubes were centrifuged, washed free of unbound MAb, resuspended in 0.5 ml plasma and labeled with $^{111}$In-Merc (2-Meroaptopyridine-N-oxide), using the method of Intenzo et al. J. Nucl. Med 28: 438–441, (1987). These were then subjected to a nylon wool adherence test according to the method of MacGregor et al. N. Engl. J. of Nucl. Med. 291: 602–606, (1974). In another set of experiments, the control cells and those exposed to the MAb, were allowed to phagocytose $^{99m}$Tc sulfur colloid. The un-engulfed $^{99m}$Tc colloid was then eliminated using the method of Schrothe Eupr. J. Nucl. Med. 6: 469–472, (1981). In each case the radioactivity associated with neutrophils was determined and compared with the control cells.

When an average of 10% of the available surface antigens were bound to anti-SSEA-1, the phagocytic ability and nylon wool adherence of human neutrophils was approximately 70% and 80% of the respective control cells. At 4% or lower antigenic saturation, no apparent changes in cell function was observed.

Interaction of labeled MAb with Neutrophils of other animal species

Anti-SSEA-1 and B.37.2.1 MAbs were labeled with $^{111}$In in the manner described herein and evaluated for interaction with neutrophils separated from blood obtained from the rat, cat, guinea pig, dog, rabbit, sheep and pig. Anti-SSEA-1 antibody did not cross-react with neutrophils from these species.

Gel electrophoresis:

To analyze the chemical form of radioactivity that remained in plasma following the incubation of $^{111}$In labeled antibodies with neutrophils in whole blood, the plasma was separated by gel electrophoresis. Ten percent polyacrylamide gel plates were prepared using the technique described by Osterman, Methods of Protein and Nucleic Acid Research, Chapter I, Springer-Verlag, Los Angeles, Calif. (1984). Twenty to fifty microliters of the supernatant was loaded into each of two wells. $^{111}$Indium chloride, $^{111}$In-DTPA, $^{111}$In transferring and $^{111}$In labeled MAb and other molecular weight markers such as albumin and trypsin inhibitor were loaded as reference in other wells.

SDS-Tris borate buffer pH 7.4 was used as the electrolyte and the electrophoresis was carried out at 250 V, for 4 hrs. The plated were then removed, the gel carefully separated, wrapped in thin plastic sheets, and frozen in a freezer. Autoradiography wa then performed using Kodak X-ray film. The gel was then cut into 0.5 cm sections and % radioactivity associated with each section was counted in an automatic gamma counter for quantification of the radioactivity associated with each peak. These were plotted as the percentage of the total radioactivity in each lane vs the distance in centimeters.

Gel electrophoretic analysis of the radioactivity remaining in plasma indicated that approximately 21%, 42% and 57%m for DTPA, ABE and BABE respectively was associated with plasma proteins with M.W. 70–80K daltons, which is in the range of the M.W. of transferrin. The radioactivity that remained in plasma as M W. 900 K daltons, probably as $^{111}$In DTPA anti-SSEA 1, $^{111}$In-ABE-anti-SSEA-1 and $^{111}$In-BABE-anti-SSEA-1, was 57%, 12% and 19% respectively.

What is claimed is:

1. A method of detecting occult abscess and inflammation in a mammal, comprising the steps:
   administering to the mammal an effective amount of a reagent comprising an antibody against stage specific embryonic antigen-1, a radiolabel and a bifunctional chelating agent which links said antibody and said radiolabel under conditions which allow the reagent to accumulate at sites of occult abscess; and
   detecting said occult abscess by radioscintigraphic method.

2. The method of claim 1 wherein said bifunctional chelating agent is cyclic anhydride of diethylenetriaminepentaacetic acid.

3. The method of claim 1 wherein radiographic method is scintillation scanning.

4. The method of claim 1 wherein said radiolabel is $^{111}$Indium, $^{99m}$Technetium, $^{67}$Gallium, $^{68}$Gallium, $^{97}$Ruthenium, $^{123}$Iodine, $^{90}$Yttrium, $^{203}$Lead, $^{67}$Copper or $^{111m}$Indium.

5. The method of claim 4 wherein said radiolabel is $^{111}$Indium or $^{99m}$Technetium.

6. A method of detecting occult abscess and inflammation in a mammal wherein a reagent containing a radiolabeled antibody is administered in an effective amount to the mammal, the reagent is allowed to accumulate at the site of the abscess and the radiolabel is then detected by radiographic method, in which method a reagent comprising an antibody against stage specific embryonic antigen-1, a radiolabel and a bifunctional chelating agent to link said antibody and said radiolabel is used.

7. The method of claim 6 wherein said bifunctional chelating agent is cyclic anhydride of diethylene triaminepentaacetic acid.

8. The method of claim 6 wherein said radiolabel is $^{111}$Indium, $^{99m}$Technetium, $^{67}$Gallium, $^{68}$Gallium, $^{97}$Ruthenium, $^{123}$Iodine, $^{90}$Yttrium, $^{203}$Lead, $^{67}$Copper or $^{111m}$Indium.

9. The method of claim 8 wherein said radiolabel is $^{111}$Indium or $^{99m}$Technetium.

10. A method of detecting occult abscess and inflammation in a mammal wherein a reagent containing an antibody linked to a chelating agent and a radiolabel is administered in an effective amount to the mammal, the reagent is allowed to accumulate at the side of the abscess and the radiolabel is then detected by radiographic method, in which method an antibody against stage specific embryonic antigen-1 is used.

* * * * *

UNITED STATES PATENT AND TRADEMARK OFFICE
CERTIFICATE OF CORRECTION

PATENT NO. : 4,917,878

DATED : April 17, 1990

INVENTOR(S) : Thakur

It is certified that error appears in the above-identified patent and that said Letters Patent is hereby corrected as shown below:

Col. 2, line 35, delete "$^{111}$Indium or $^{111}$Indium" and insert -- $^{111}$Indium or $^{111v}$Indium --.

Col. 2, line 51, delete "an" at the end of the line.

Col. 4., line 4, delete "Anti-stage specific embryonic antigen-1 antibody" and insert -- Antibody against SSEA-1 --.

Col. 7, line 41, Following "acted" insert -- DTPA --.

Col. 7, line 50, delete "the" and insert -- then --.

Col. 9, line 4, delete "$^{99v}$TcO$_4$$^{31}$" and insert -- $^{99v}$TcO$_4$ --.

Col. 9, line 16, delete "as" and insert -- was --.

Col. 10, line 22, delete "wa" and insert -- was --.

Col. 10, line 36, delete "mw." and insert -- m.w. --.

UNITED STATES PATENT AND TRADEMARK OFFICE
CERTIFICATE OF CORRECTION

PATENT NO. : 4,917,878

DATED : April 17, 1990

INVENTOR(S) : Thakur

It is certified that error appears in the above-identified patent and that said Letters Patent is hereby corrected as shown below:

Col. 10, line 37, delete "SSEA 1" and insert --SSEA-1--.

Signed and Sealed this

Twenty-first Day of April, 1992

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,917,878
DATED : April 17, 1990
INVENTOR(S) : Madhukar L. Thakur It is certified that error appears in the above-identified patent and that said Letters Patent is hereby corrected as shown below:

On title page, item [22], delete

[May 2, 1988] and insert therefor --April 29, 1988--.

Signed and Sealed this

Ninth Day of March, 1993

Attest:

STEPHEN G. KUNIN

Attesting Officer

Acting Commissioner of Patents and Trademarks